United States Patent [19]

Ohnishi et al.

[11] Patent Number: 4,855,057
[45] Date of Patent: Aug. 8, 1989

[54] REGENERATION TYPE BODY FLUID TREATING CIRCUIT AND METHOD FOR TREATING BODY FLUID

[75] Inventors: Michikazu Ohnishi, Kobe; Hiroshi Ohgoshi, Settsu; Satoshi Takada, Kobe, all of Japan

[73] Assignees: Yokogawa Electric Corporation, Tokyo; Kanegafuchi Kagaku Kogyo Kabushiki Kaisha, Osaka, both of Japan

[21] Appl. No.: 190,985

[22] Filed: May 6, 1988

Related U.S. Application Data

[62] Division of Ser. No. 102,691, Sep. 29, 1987.

[30] Foreign Application Priority Data

Sep. 30, 1986 [JP] Japan .................. 61-234200
Oct. 3, 1986 [JP] Japan .................. 61-236783

[51] Int. Cl.⁴ .................. B01D 13/00; B01D 15/00
[52] U.S. Cl. .................. 210/650; 210/670; 210/782; 210/797; 210/806
[58] Field of Search ............ 210/649, 650, 663, 670, 210/681, 739, 782, 787, 790, 791, 794, 797, 806, 798; 604/4, 5, 6, 64

[56] References Cited

U.S. PATENT DOCUMENTS 4,696,670 9/1987 Ohnishi et al. .................. 604/4

FOREIGN PATENT DOCUMENTS 0181741 5/1986 European Pat. Off. .
61-119271 6/1986 Japan .
61-162953 7/1986 Japan .
61-164562 7/1986 Japan .

Primary Examiner—W. Gary Jones
Attorney, Agent, or Firm—Armstrong, Nikaido, Marmelstein, Kubovcik & Murray

[57] ABSTRACT

A body fluid treating circuit comprising a block for collecting a body fluid from a human body, a body fluid treating block and a block for returning the treated body fluid to the human body, said body fluid treating block comprising a plurality of treating units for treating the body fluid by passing therethrough, the units being arranged in parallel flow relationship, body fluid feed and return lines connected to each of the treating units so as to selectively feed to and return from the units through line switching means. The body fluid is treated using the above circuit by a method wherein the body fluid is fed to at least one first treating unit among a plurality of treating units to treat it up to a predetermined volume and the feeding is then switched to the residual second treating unit or units, the regeneration and washing of the first unit are conducted by successively feeding the regenerating liquid and washing liquid while treating the body fluid in the second unit, and after the completion of the treatment in the second unit, the body fluid feed line is switched to the regenerated and washed first unit with confirmation of the salt concentration of the effluent therefrom by the salt concentration measuring means in order to conduct the treatment in the first unit during which the regeneration and washing of the second unit are conducted, the above procedures being further repeated as occassion demands.

4 Claims, 10 Drawing Sheets

F I G . 4
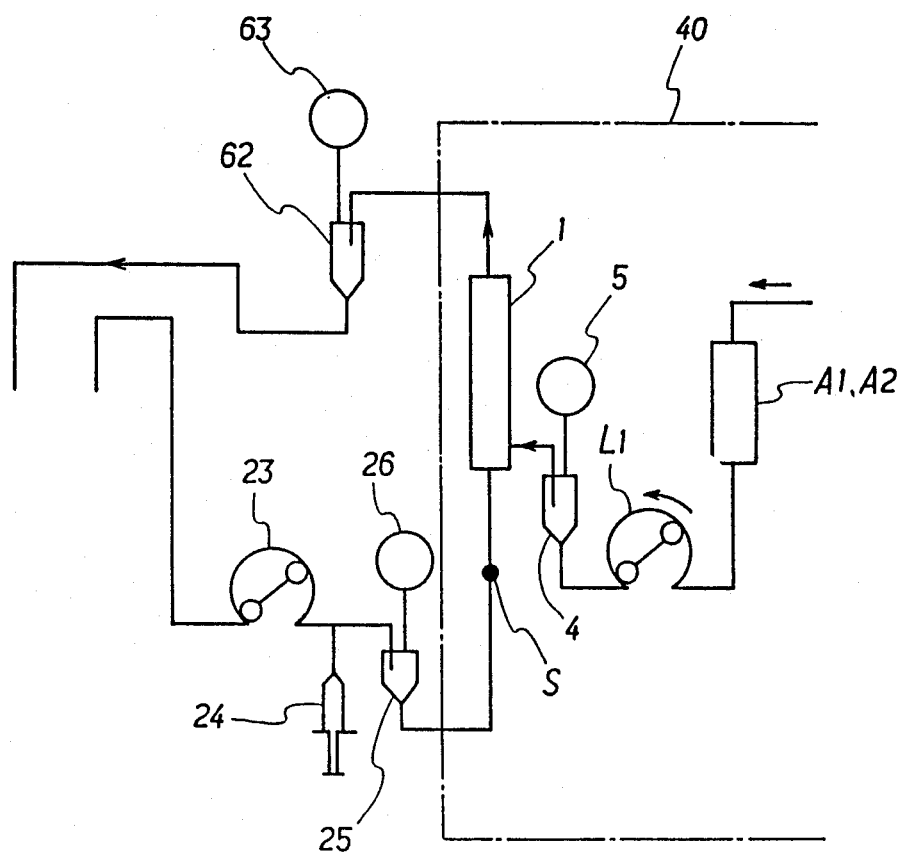

REGENERATION TYPE BODY FLUID TREATING CIRCUIT AND METHOD FOR TREATING BODY FLUID

This is a division of application Ser. No. 102,691 filed Sept. 29, 1987.

BACKGROUND OF THE INVENTION

The present invention relates to a body fluid treating apparatus used in a body fluid treating circuit wherein the blood or other body fluid is withdrawn from the human body, subjected to an appropriate treatment with a treating device and returned to the human body, and a method for treating body fluid. More particularly, the present invention relates to the treating apparatus and method comprising the use of a plurality of treating devices which are sequentially and alternately put into a treatment mode in such a manner that while one of the devices is on the treatment mode, the other devices are on a regeneration mode, with the switching of any of the devices from one mode to the other being effected safely and surely.

The term "body fluid" as used herein means any fluid matters, including blood, lymph and ascites, that exist in the human body.

The term "body fluid treatment" as used herein means application of a treatment to body fluids, e.g. removal of harmful or unnecessary components, addition of medicinally effective substances, supplementation of deficient components, substitution of one component with another.

A method of treating a body fluid in which the body fluid is withdrawn from a human body, extracorporeally treated and returned to the body, namely a so-called extracorporeal circulation treatment, has heretofore been applied to treatment of various diseases. For example, this treatment is effective for hyperlipidemia, drug intoxication, fulminant hepatitis, macroglobulinemia, multiple myelitis, serious akinesia, rheumatoid arthritis, hepatic failure, lupus erythematosus, nephritis and other diseases.

FIG. 5 is a schematic view showing a conventional body fluid treating circuit used for selective removal of low-density lipoprotein (LDL) and very-low-density lipoprotein (VLDL), which are chief etiologic factors in hyperlipidemia, from blood of a patient with hyperlipidemia. This body fluid treating circuit is composed of blood collection block 20, blood treatment block 40, and blood return block 60.

In the blood collection block 20, there are disposed collected blood pressure gage 21, blood pressure abnormality detector 22, blood collection pump 23, anti-coagulant pump 24 for heparinization, drip chamber 25, plasma separation pressure gage 26 and so on, so that the blood collection may be performed continuously and safely. In addition, supply source 27 for a circuit washing liquid (e.g. physiological saline or Ringer's solution) and liquid discontinuation sensor 28 are connected in position near the blood collection end.

The treatment block 40 where blood is subjected to a predetermined treatment, includes plasma separator 41, plasma pressure gage 42, blood leak detector 43, plasma pump 44, supply side drip chamber 45, supply blood pressure gage 46, treating device 47 for removal of LDL and VLDL from the plasma, filter 48 for preventing incorporation of adsorbent, etc., return side drip chamber 49, and delivery blood pressure gage 50, and so on.

In the body fluid return block 60, there are disposed heating bag 61, drip chamber 62, return blood pressure gage 63, and air bubble detector 64 so that the treated blood may be safely returned to human body 70.

The treatment with the above body fluid treating circuit is explained below.

First, from the patient's body 70, the blood is withdrawn by the blood pump 23, while a proper blood collection pressure is maintained. While the anti-coagulant heparin is infused from the anti-coagulant pump 24 into the blood, the collected blood is guided to the plasma separator 41. In this plasma separator 41, a portion of all of the plasma fraction of the blood is separated and sent to the treating device 47, while the remainder of the blood flows along. The treating device 47 is packed with an adsorbent which adsorbs to remove LDL and VLDL in the separated plasma while it flows through the device. The treated plasma is joined together with the blood cell fraction which has passed through the plasma separator 41, and the mixed blood is warmed to a suitable temperature in the heating bag 61 before being returned to the human body.

However, in clinical use, the above body fluid treating circuit has the following disadvantages.

(i) During blood treatment, the entire circuit is full of the blood. This means that a substantial quantity of blood is taken outside the patient's body. Since this condition may cause anemia, there is a certain limitation in the scaling-up of the treating device.

(ii) Since the amount of extracorporeal circulation of the blood is large, the treatment can hardly be applied to underweight, anemic, or hypotensive patients.

(iii) As a preparatory procedure for body fluid treatment, circuit elements are assembled and the circuit is washed with physiological saline or the like by passing through it. Therefore, before start of the treatment, the circuit is in the state of being full of the washing liquid. As the treatment proceeds, the washing liquid enters into the patient's body, thus it tends to reduce the colloid osmotic pressure of the blood which may cause a blood pressure drop.

In order to solve the above disadvantages, the present applicant proposed a body fluid treating circuit in which a plurality of treating devices with a reduced capacity than conventional one are provided, as disclosed in Japanese Patent Publication Kokai No. 164562/1986. FIG. 6 shows the treatment zone in the proposed circuit. A plurality of small treating devices 51, 52 are installed in parallel within the treatment zone and these small devices 51, 52 are equipped with a body fluid sending out system including washing liquid supply source 53 and delivery pump 54, and a washing liquid discharge line 55. In this arrangement, by operating these small devices 51, 52 in turn, the extracorporeal circulation volume of the blood can be decreased. Moreover, by withdrawing the pre-filled washing liquid from the small treating devices 51, 52 through the discharge line 55 before starting the treatment, the drop in colloid osmotic pressure can be prevented. The above body fluid treating circuit can overcome the abovementioned disadvantages (i) to (iii).

However, the above proposed body fluid treating circuit is still inadequate and has the following disadvantage.

(iv) Although the extracorporeal circulation volume of blood and the volume of inflow of the washing liquid into the human body are both decreased, the total amount of adsorbent required per treatment remains unchanged. Therefore, if one tries to reduce the capacity of each small treating device, an increased number of small treating devices has to be provided. Moreover, since such small treating devices are discarded after use, it is inevitable to incur an increased equipment cost and, hence, an increased cost of medical treatment.

In Japanese Patent Publication Kokai No. 162953/1986, the present applicant disclosed a technique for regenerating the adsorption ability of the used adsorbent, wherein after LDL and VLDL are adsorbed by an adsorbent composed of a water-insoluble support such as cellulose and a polyanion compound, such as dextran sulfate, immobilized onto the support, the adsorbent is washed with a highly concentrated aqueous solution of an electrolyte (0.18 to 6 moles/liter) to elute the LDL and VLDL.

When this regeneration method is applied to the above proposed body fluid treating circuit, one may alternately and repeatedly operate a plurality of small treating devices provided in the treatment zone by regenerating the used treating device while the body fluid is treated by the other device. This means that the number of small treating devices can be held to the necessary minimum and, therefore, the above-mentioned disadvantage (iv) can be eliminated.

However, when this regeneration technique is applied to the above-mentioned body fluid treating circuit using a plurality of small treating devices, the following new problem is encountered. That is, the aqueous electrolyte solution (regenerating liquid) for regeneration of the adsorbent contains electrolytes in concentrations higher than the physiological saline and, if it comes into contact with body fluids, the salt concentrations of the body fluids are inevitably increased. Moreover, if the regenerating liquid remains in the device, it would inflow into the patient's body to cause various disturbances.

SUMMARY OF THE INVENTION

The present invention provides a body fluid treating circuit and a method of treating body fluids, which are characterized in that a plurality of treating devices are provided in a body fluid treating circuit and are rendered re-usable by sequential regeneration of the devices, and upon the reuse of the devices it is checked to assure that there is no residual regenerating liquid in the treating devices and, if the residual regenerating liquid is found, the treatment of the body fluids is discontinued.

The treating block of the body fluid treating circuit according to the present invention comprises a plurality of treating devices, body fluid feed and in return lines connected to the respective treating devices in parallel, regenerating liquid feed and return lines connected to the respective treating devices in parallel, washing liquid feed and return lines connected to the respective treating device in parallel, means for measuring the salt concentration of the effluent washing liquid from the respective treating devices, a confirmation line for guiding the effluent washing liquid to the means for measuring the salt concentration, flow rate regulating means for the body fluid, regenerating liquid and washing liquid, and switching means for switching the respective lines. When the volume of the body fluid treated in a first treating device has reached a predetermined level, the treating operation is switched to a second treating device, and then the regeneration of the first device and the treatment of body fluid by the second device are carried out concurrently. On completion of regeneration of the first device, the washing liquid is supplied to this first device and the salt concentration of the effluent washing liquid is measured. When the volume of the body fluid treated by the second device has reached a predetermined level, the treating operation is switched back to the regenerated first device with confirmation that the salt concentration of the effluent washing liquid from the first device is not more than the predetermined level. Preferably, the circuit is further provided with means for controlling the actuation of the line switching means in a sequential timed manner so as to perform the above procedures.

In accordance with the present invention, the respective treating devices can be regenerated and reused, thus the capacity of each treating device required for treating a given volumn of body fluid can be decreased as compared with the conventional device. In other words, when the treating device is designed to have the same capacity as the conventional device, the volume of body fluid that can be treated is increased in comparison with the conventional treating circuit. Moreover, after confirming that the regenerating liquid does not remain in the treating device by monitoring the salt concentration in the effluent washing liquid from the treating device which has undergone a regeneration cycle, the switching of the treating devices is conducted so that the risk of entry of the washing liquid into the human body is avoided.

BRIEF DESCRIPTION OF THE DRAWINGS

In the accompanying drawings, FIGS. 1 to 4 show embodiments of the present invention and FIGS. 5 and 6 show conventional body fluid treating techniques. In the drawings;

FIG. 1 is a schematic circuit diagram showing the treating block of a body fluid treating circuit;

FIG. 3 is a circuit diagram showing another embodiment of the present invention;

FIG. 4 is a schematic circuit diagram showing an embodiment of recovery of blood cells;

FIG. 5 is a circuit diagram showing a conventional body fluid treating circuit; and FIG. 6 is a circuit diagram showing the treating block of another conventional body fluid treating circuit.

DETAILED DESCRIPTION

The invention will be described with reference to an embodiment as applied to the treatment of blood for removal of LDL or VLDL, but it is to be understood that the invention can be applied to various body fluid treatments.

Figure 1:
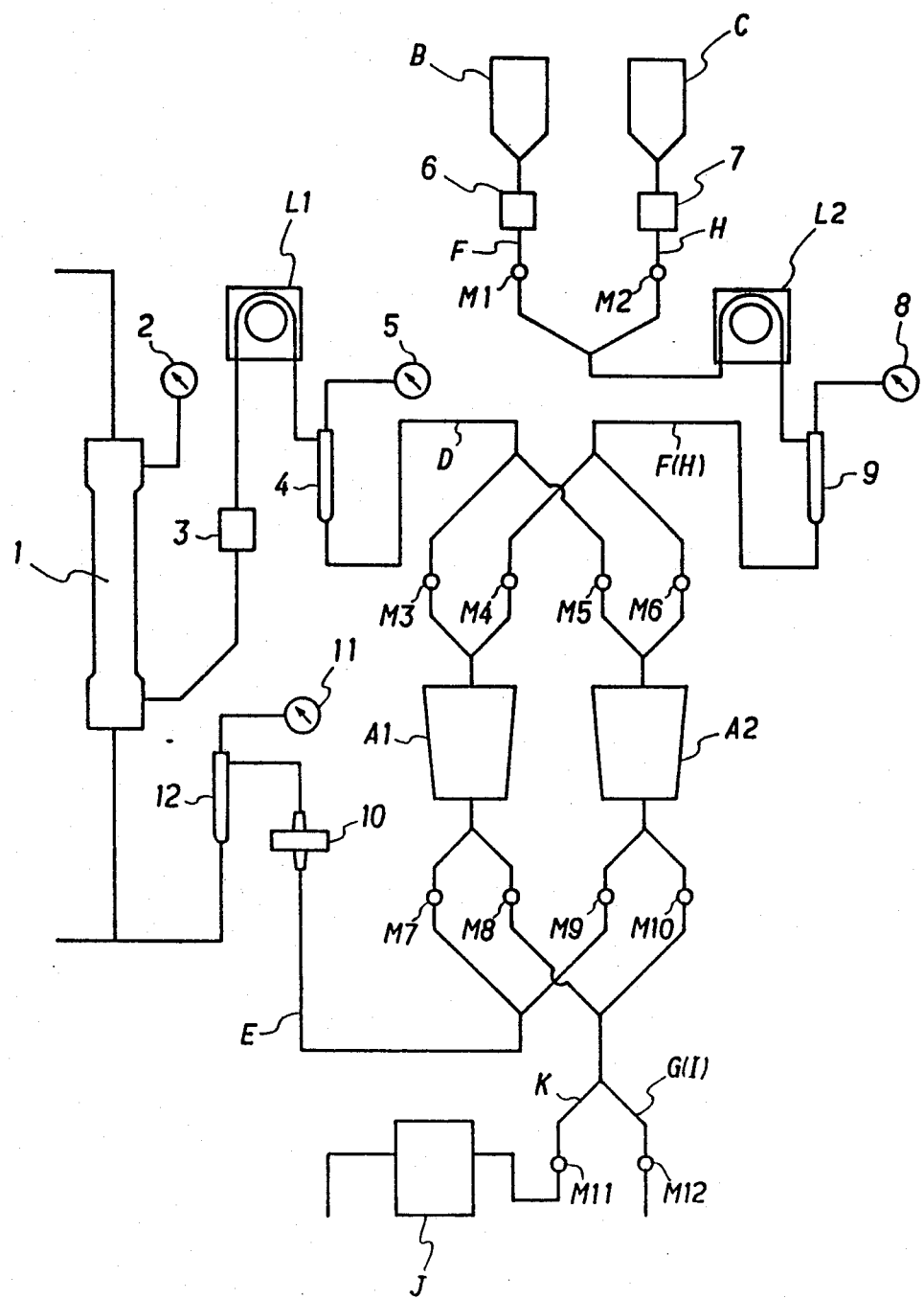

Referring to FIG. 1 which is a circuit diagram of the treatment block of a body fluid treating circuit according to the invention, the treatment block includes a couple of treating units or devices A1 and A2 each having the same treating capacity. Each of the treating units A1 and A2 connected in parallel is charged with an adsorbent capable of selectively adsorbing LDL or VLDL from the blood. Also provided in this block are a source B for supply of a regenerating liquid adapted to regenerate the treating ability of the units A1, A2 and a source C for supply of a washing liquid for forcing out the body fluid or regenerating liquid from each treating unit. Connected to the upstream side of each of the treating units A1 and A2 are a body fluid feed line D, a regenerating liquid feed line F and a washing liquid feed line H. In this embodiment, the regenerating liquid feed line F is joined with the washing liquid feed line H at a position before reaching the treating units. Similarly, connected to the downstream side of each of the treating units A1 and A2 are a body fluid return line E and a discharge line G(I) which serves as a regenerating liquid discharge line and a washing liquid discharge line. For each of the above lines, a plurality of lines or a line having branches can be used. Branching out of the discharge line G(I) is a confirmation line K, through which the effluent washing liquid discharged from the treating unit A1 or A2 is guided to a salt concentration measuring means J. Also, provided in this treating apparatus are a body fluid conveying pump L1 adapted to control the flow rate of body fluid and a liquid supply pump L2 adapted to control the flow rate of the regenerating liquid or washing liquid. At appropriate positions in the lines, valves M1 to M12 are provided, thereby controlling the switching of flow passages for the body fluid, regenerating liquid or washing liquid.

Further, in this embodiment, there are provided a plasma separator 1 to separate the plasma fraction from the blood to be treated, a plasma pressure gage 2, a blood leak monitor 3 for alerting the operator to the entry of blood corpuscles into the plasma, a supply side drip chamber 4 to prevent entry of air bubbles, a feed plasma pressure gage 5, liquid discontinuation sensors 6 and 7, a feed liquid pressure gage 8, a drip chamber 9 in the regeneration system, a filter 10 for preventing entry of the adsorbent into the plasma, a return plasma pressure gage 11, and a return side drip chamber 12.

The plasma separator 1 includes a separation membrane to separate and extract the plasma fraction from the blood. However, the blood corpuscles are liable to adhere to the separation membrane and, once deposited, cannot be readily detached.

Since the corpuscles play particularly important rolls, the loss thereof should be minimized in the treatment. The corpuscles remaining in the plasma separator has hitherto been recovered by passing physiological saline through the separator after completion of treatment. However, a thorough recovery of corpuscles demands the use of a large quantity of physiological saline, and when such a large quantity of saline is used, there occurs a sudden increase in the intracorporeal circulation to induce a decrease in colloid osmotic pressure, a change in blood pressure and other adverse effects due to blood dilution such as anemia.

Figure 5:
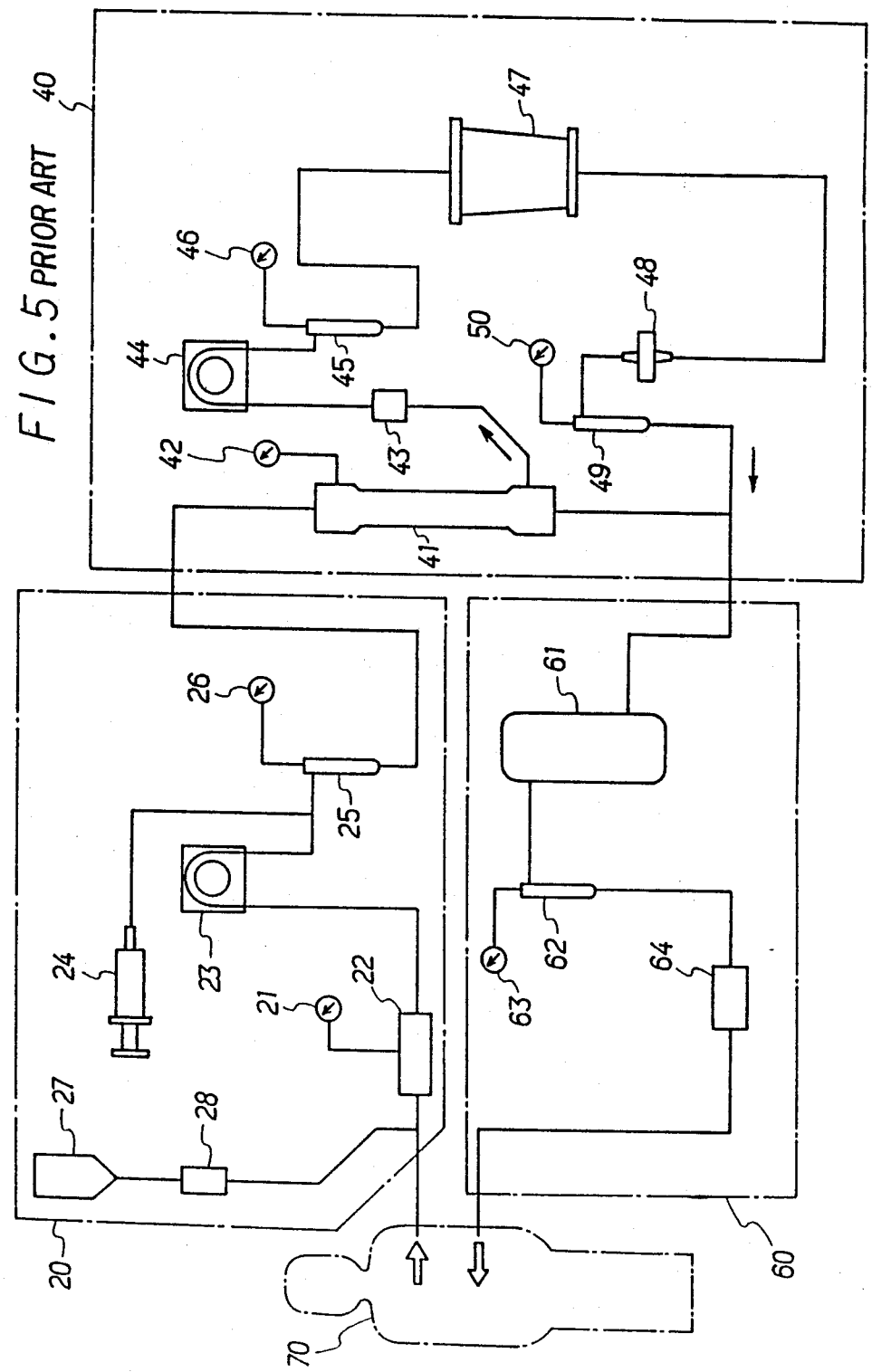
Figure 6:
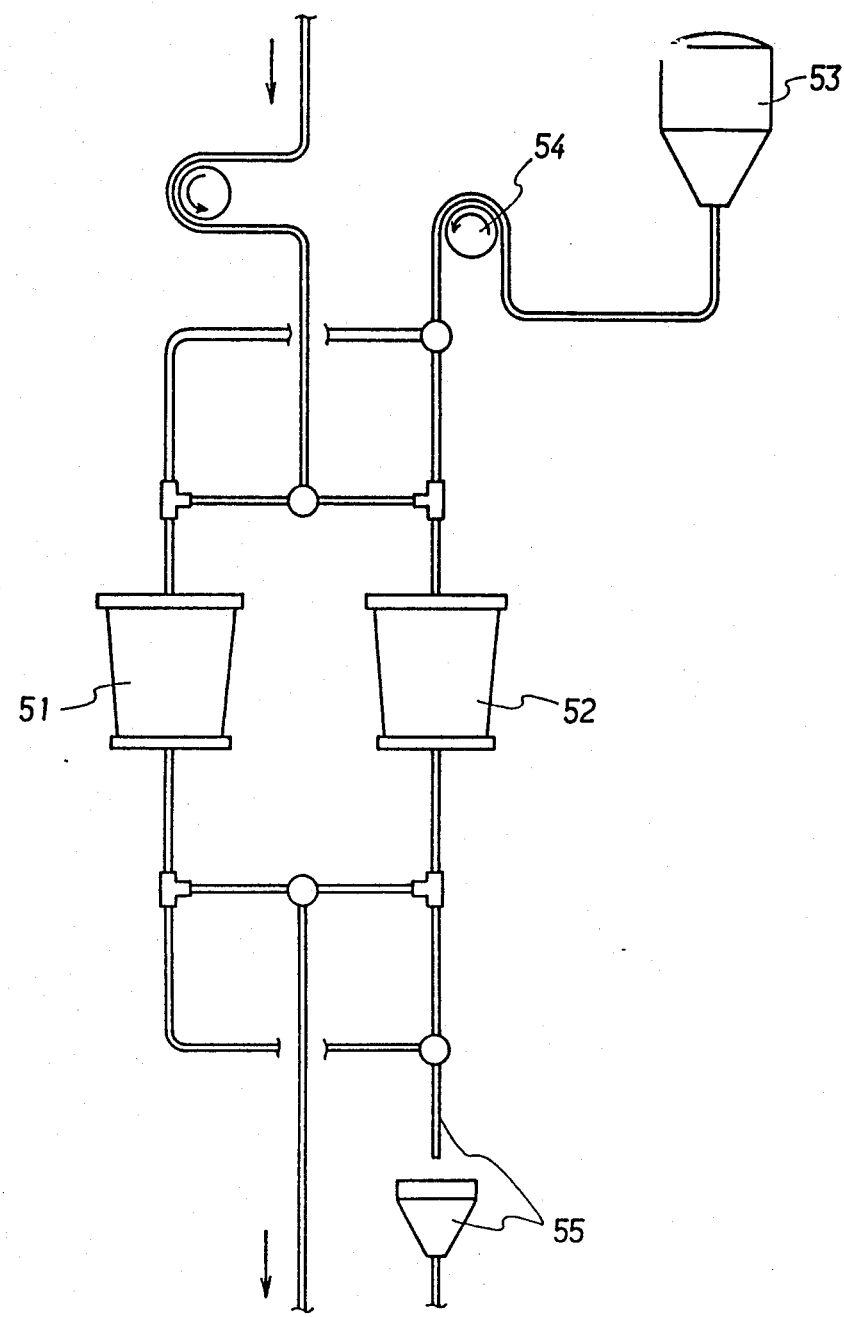

To avoid these disadvantages, the blood cell recovery technique illustrated in FIG. 4 is beneficial. In FIG. 4, like reference characters denote like parts in FIGS. 1 and 5. FIG. 4 is a view to illustrate a method for recovery of blood cells from the plasma separator 1, where the treating units A1 and A2 are represented as a single block for convenience's sake. After the treatment, the plasma fraction remaining in the treating block 40 is guided to the plasma separator 1 so as to pass in the direction reverse to the plasma separation direction, whereby the blood cells adhering to the membrane are released and recovered. To be specific, the plasma separator 1 is shut off at a suitable place S on the side where the collected blood enters into the separator, and at the same time, the body fluid pump L1 is driven in the reverse direction to send back the plasma fraction remaining in the treating unit A1 or A2 and other treating block circuit to the plasma separator 1 where it undergoes reverse osmosis to thereby recover the blood corpuscles from the membrane. Since the plasma fraction which has a high affinity for the corpuscles, is utilized as a medium for recovery of corpuscles in the above method, the ability of releasing the corpuscles from the separation membrane is far higher than physiological saline and, therefore, the volume of plasma required for this purpose is small as compared with saline and there is no adverse effect on the human body. In addition, since this medium for recovery of corpuscles is the plasma fraction of the patient's own blood, there is no risk of adverse influence on the blood components.

The total capacity of the above-mentioned treating units A1 and A2 may be less than one-half of the capacity of a single treating unit conventionally used. The reason is that although the capacity of removing LDL and VLDL from the plasma depends on the total amount of adsorbent used, the regeneration and reuse of the treating units enables to reduce the amount of adsorbent required because of increase in the total amount of adsorbent utilized for the treatment.

The regenerating liquid is selected according to the adsorbent used. In case of an adsorbent composed of a water-insoluble support and a polyanion compound, immobilized thereto, capable of adsorbing harmful substances in the blood such as LDL and VLDL, aqueous solutions of electrolytes in high concentrations are used as the regenerating liquid. Examples of the electrolytes are, for instance, sodium chloride, potassium chloride, calcium chloride, sodium phosphate, potassium phosphate, sodium carbonate, potassium carbonate, and the like. For instance, when the adsorbent is a dextrane-immobilized cellulose gel, an aqueous solution of sodium chloride having a concentration of 0.18 to 6 moles/liter, especially 0.3 to 1 mole/liter, is preferably used.

Physiologically harmless liquids, e.g. Ringer solution and physiological saline (salt concentration: about 0.15 mole/liter), can be used as the washing liquid in the present invention. It is necessary that the washing liquids are physiologically harmless, because they may come into contact with the body fluids or may flow into the human body.

The salt concentration measuring means J is intended to confirm that the salt concentration of the effluent from the treating unit is equal to the physiological salt concentration, and may for example be a conductivity meter, although this is not an exclusive choice. Any devices or means which can attain this purpose can be used.

The plasma separator 1 may be of any of the known types, e.g. a membrane separator using a semi-permeable membrane for blood filtration or a centrifugal plasma separator which utilizes a difference in sedimentation constant.

The valves M1 to M12 may each be a clamp, a pinch cock or the like. A solenoid pinch cock is preferred in that it is simple in construction and control. When the solenoid pinch cock is such that it is open when current flows and closed when current does not flows, accidents in emergencies such as an interruption of current can be prevented. Further, accident due to an erratic operation can be prevented when the action of the pinch cock is detected by an appropriate sensor.

A method for treating a body fluid using the above-mentioned treating circuit will be explained with reference to FIG. 2(A) to 2(J). In the drawings, the open condition of any of valves M1 to M12 is indicated by white dot ○ and the closed condition by black dot ●. Further, any circuit line in which a liquid such as a body fluid is flowing is indicated by a solid line, while any circuit line in which no liquid is flowing is indicated by a broken line. As to the order of use of the treating units, A1 is the pre-stage unit and A2 is the post-stage unit.

Figure 2B:
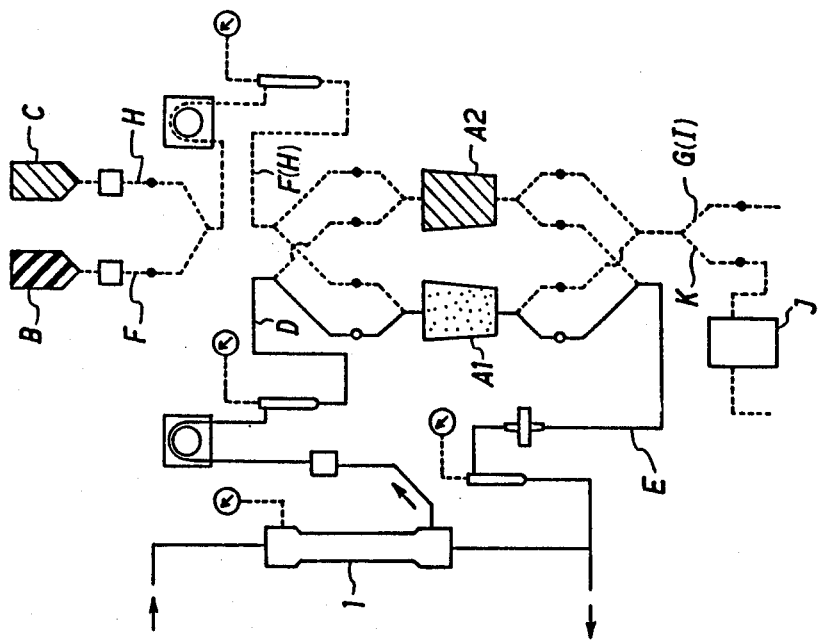
FIGS. 2(A) to 2(J) show circuit diagrams illustrating respective steps of a body fluid treating method.
Figure 2A:
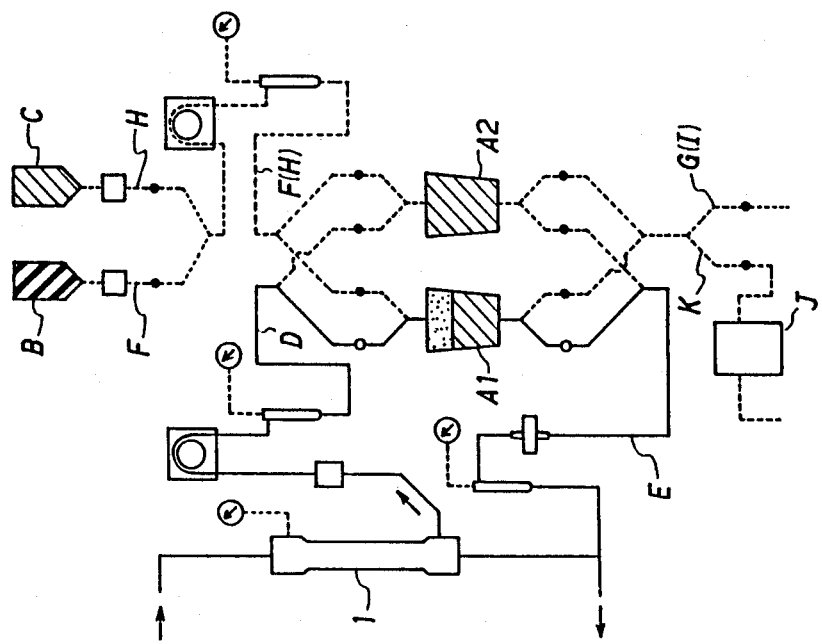

(1) [Refer to FIG. 2(A)]

First, the blood withdrawn from the human body is guided to plasma separator 1 where the plasma fraction is separated from the blood. The plasma so separated is fed to pre-stage treating unit A1 through body fluid feed line D. Since, as stated above, the treating units A1 and A2 are filled with a washing liquid such as physiological saline used in a washing step prior to the treating step, the introduction of the plasma drives out this washing liquid from the treating unit A1. The volume of the treating unit used in the invention is far smaller than that of a conventional treating unit and, therefore, the infusion of the washing liquid in a volume corresponding to the volume of one treating unit into the human body does not cause any trouble. Thus, only at the start of the treatment procedure, the washing liquid is guided to the body fluid return line E and joined with the concentrated blood immediately following separation of the plasma. Since the return of the concentrated blood as it is to the human body may cause a trouble to the body, it is rather preferred to infuse this effluent washing liquid from the treating unit A1 into the body. However, the washing liquid forced out by the introduction of plasma into the unit A1 may be guided to the withdrawal line G(I) for discharge from the circuit, as occasion demands.

(2) [Refer to FIG. 2(B)]

After the treating unit A1 has been filled with the plasma, a further amount of plasma is subsequently fed into the treating unit A1 for treatment. The treated plasma is joined with the blood which had passed through the plasma separator 1 and returned to the human body.

Figure 2D:
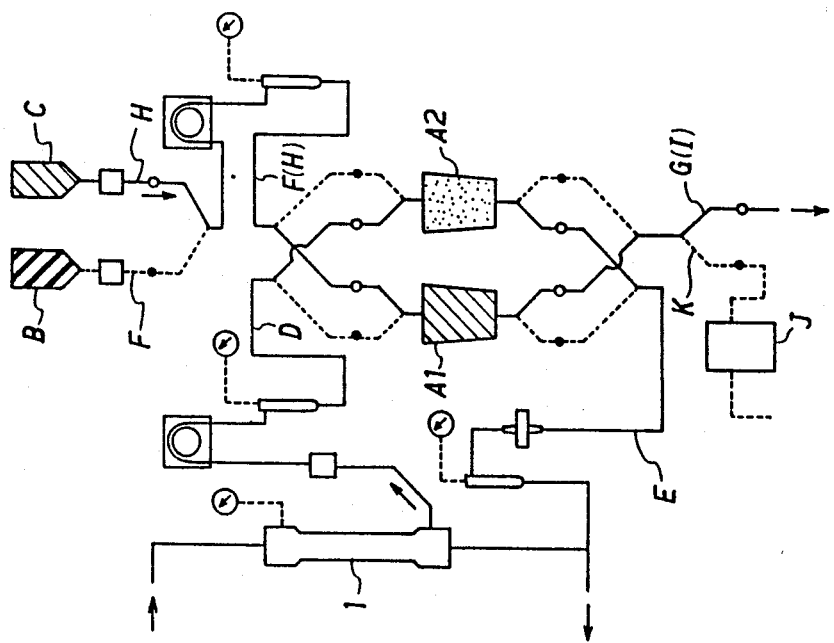
Figure 2C:
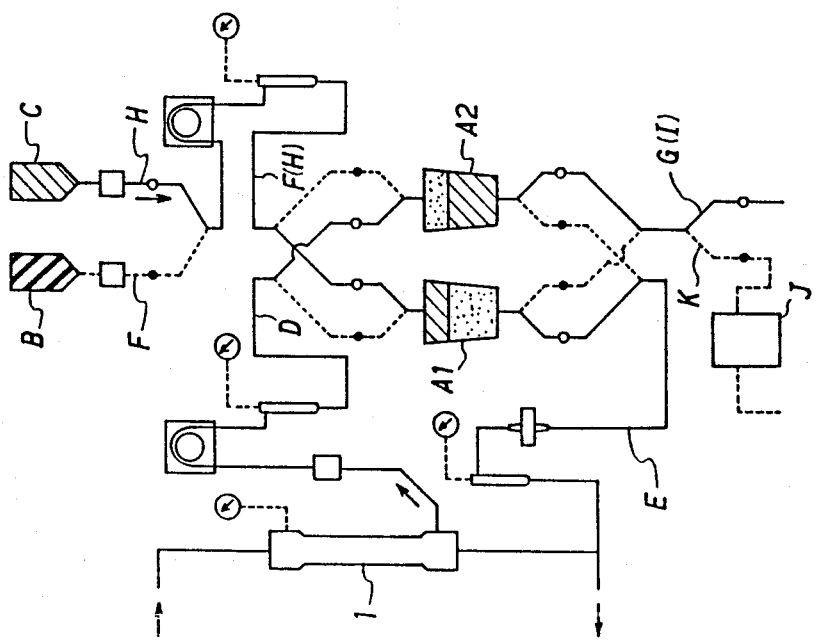

(3) [Refer to FIG. 2(C)]

When the amount of the body fluid treated in the treating unit A1 has reached a predetermined level, the supply of plasma is switched to post-stage treating unit A2 and the passage on the downstream side of the treating unit A2 is connected to the discharge line G(I). Simultaneously, the washing liquid is fed to the pre-stage treating unit A1 from washing liquid feed source C through line H, whereby the plasma in the unit A1 is forced out by the washing liquid and returned to the human body, while the washing liquid in the post-stage treating unit A2 is forced out and discharged from the circuit by the plasma introduction. In order that the blood collection rate and the blood return rate are kept constant, it is preferable to ensure that the plasma feed rate is equal to the washing liquid feed rate.

(4) [Refer to FIG. 2(D)]

After the plasma has been forced out from the pre-stage treating unit A1, the passage on the downstream side of the unit A1 is switched into communication with the discharge line G(I). On the other hand, after the washing liquid is forced out from the post-stage treating unit A2, the passage on the downstream side of the post-stage unit A2 is switched into communication with the body fluid return line E, thus the treatment by the post-stage treating unit A2 is conducted.

Figure 2F:
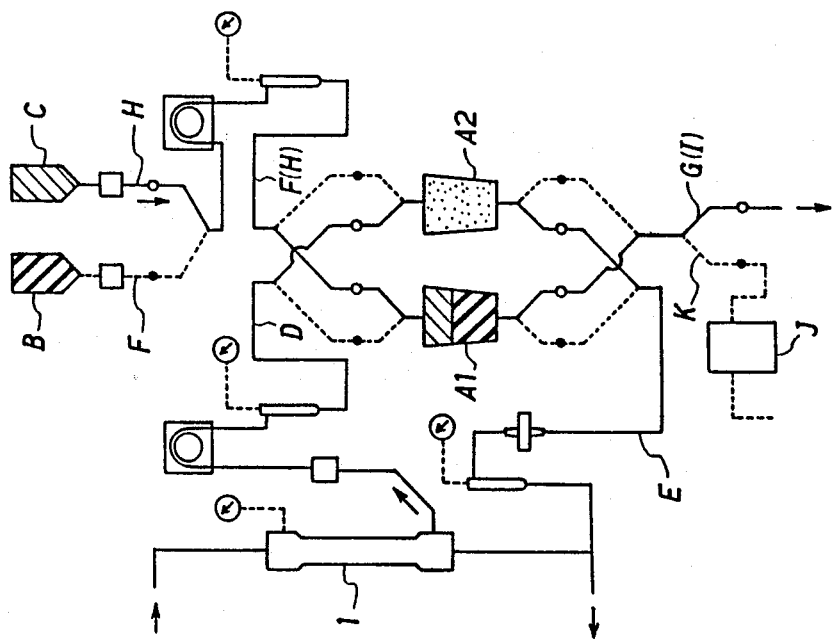
Figure 2E:
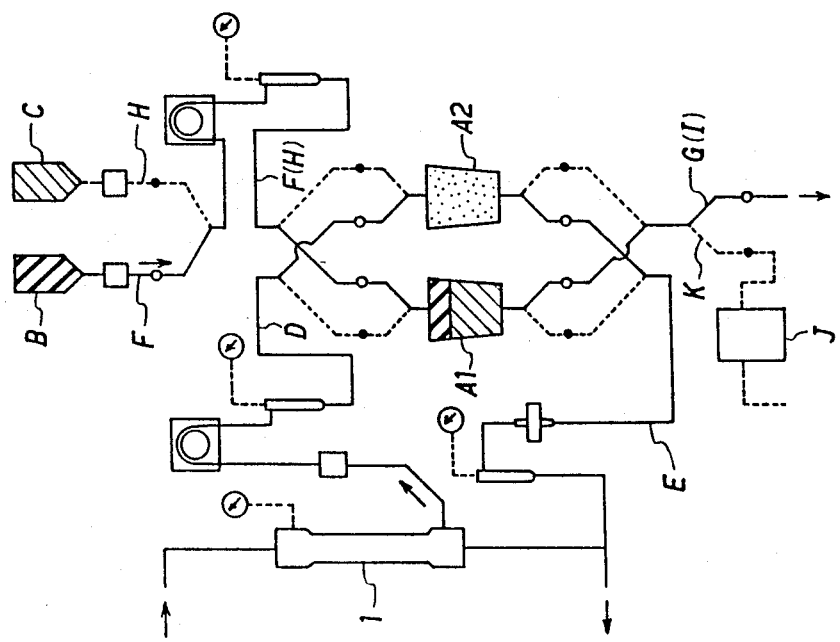
Figure 2H:
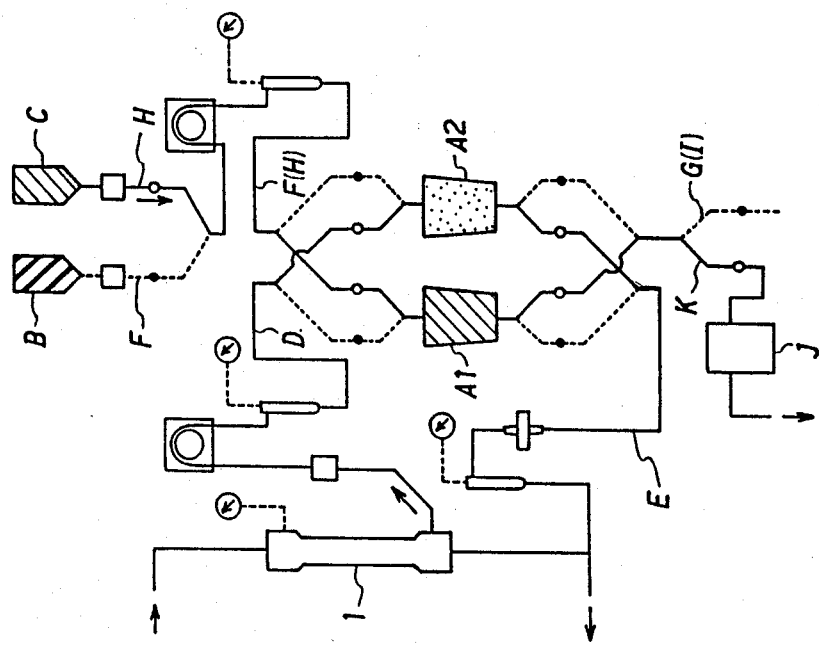

(5) [Refer to FIG. 2(E)]

Simultaneously with the treatment operation by the post-stage treating unit A2, a predetermined amount of a regenerating liquid is fed to the pre-stage treating unit A1 from regenerating liquid feed source B through line F. When the adsorbent is a cellulose gel carrying dextran sulfate as immobilized thereto and the regenerating liquid is a 0.7 mole/liter aqueous sodium chloride solution, the optimum volume of the regenerating liquid for recovery of treating ability is approximately 70% of the volume of the treating unit. The washing liquid forced out from the unit A1 by the regenerating liquid is discharged from the circuit via discharge line G(I). In this step, LDL and VLDL are eluted from the adsorbent, whereby the treating ability of the adsorbent is restored.

(6) [Refer to FIG. 2(F)]

Upon completion of feed of a predetermined amount of regenerating liquid, the passage on the upstream side of the treating unit A1 is switched into communication with the washing liquid feed line H, thus the regenerating liquid in the unit A1 is forced out by the introduction of the washing liquid and is discharged from the circuit through the line G(I).

Figure 2G:
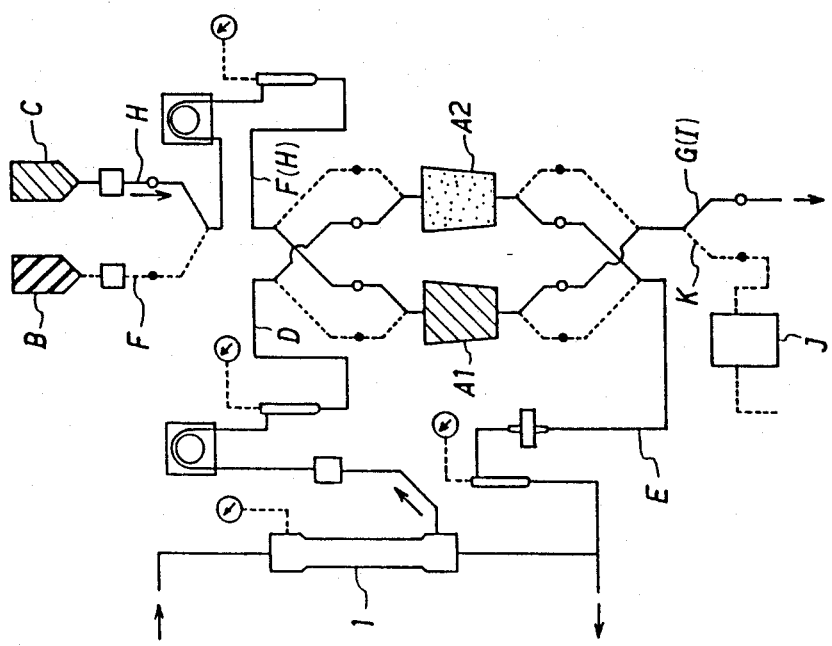

(7) [Refer to FIG. 2(G)]

After withdrawal of the regenerating liquid from the treating unit A1, the unit A1 is washed with a further supply of the washing liquid to lower the salt concentration to the physiological concentration. When the regenerating liquid is the above-mentioned 0.7 mole 1 aqueous solution of sodium chloride and the washing liquid is a physiological saline, it is preferable to pass the washing liquid in an amount of 1.5 to 2 times the volume of the treating unit.

(8) [Refer to FIG. 2 (H)]

After feeding the predetermined amount of the washing liquid to the unit 1, the passage on the downstream side of the treating unit A1 is switched into communication with the confirmation line K so as to guide the effluent washing liquid from the treating unit A1 to salt concentration measuring means J, while continuing the supply of washing liquid. The regenerating liquid flowing out of the treating unit and the washing liquid discharged just after withdrawal of the regenerating liquid from the unit contain protein components such as LDL and VLDL which were eluted from the adsorbent. If such liquids containing the proteins are fed to the salt concentration measuring means J, which may for example be a conductivity meter, its sensor part will be contaminated to detract from the accuracy and reliability of the measuring means. Therefore, to the salt concentration measuring means J is supplied the washing liquid discharged from the unit after the completion of the washing procedure, which is substantially free of proteins as stated above.

Figure 2J:
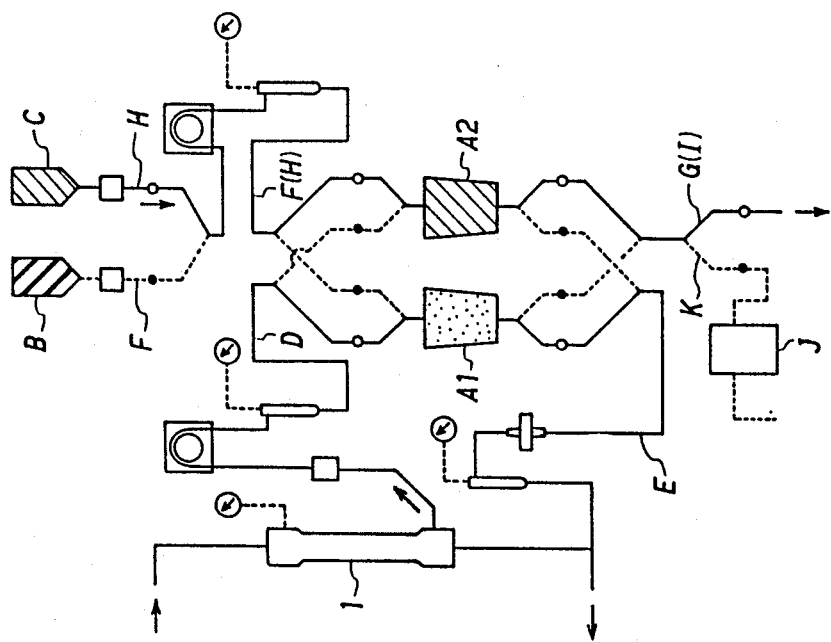
Figure 2I:
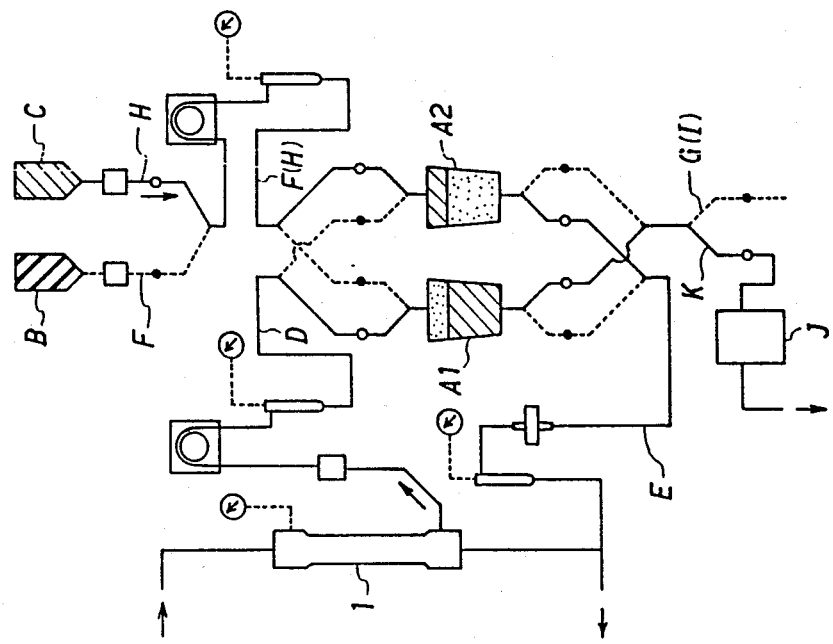

(9) [Refer to FIG. 2(I)]

When the amount of the body fluid treated by the post-stage treating unit A2 has reached the predetermined level, the supply of the plasma is switched to the pre-stage treating unit A1 with confirmation that the salt concentration of the effluent washing liquid from the unit A1 is equal to the physiological concentration, and simultaneously the route of feed of the washing liquid is switched to the post-stage treating unit A2. The salt concentration in the treating unit A1 decreases gradually as the prior washing step proceeds, and reaches the physiological concentration level by the end of the washing step. However, if it is found that the salt concentration has not dropped to the physiological level, the switching of the plasma feed line D is not performed in order to further continue the washing of the unit A1, or the treatment of the body fluid is discontinued. By the above switching operation, the plasma in the post-stage treating unit A2 is forced out by the washing liquid and returned to the human body. The washing liquid in the pre-stage treating unit A1 is forced out by the plasma and discharged out from the circuit. The plasma feed rate is preferably kept equal to the washing liquid feed rate.

(10) [Refer to FIG. 2(J)]

When the washing liquid has been discharged from the treating unit A1 by replacement with the plasma, the passage on its downstream side is switched into communication with the body fluid return line E to conduct the treatment by the treating unit A1 again. At the same time, when the body fluid is sent out of the treating unit A2 and the unit A2 has been filled with the washing liquid, the passage on the downstream side of the unit A2 is switched into communication with the discharge line G(I). (11) When the pre-stage unit A1 and the post-stage unit A2 are used alternately and repeatedly, the regeneration of the post-stage unit A2 is carried out simultaneously with the execution of the above treatment by the unit A1 in preparation for the next treating operation by the unit A2.

According to the present invention, as stated above, treating devices or units can be reused and, moreover, line switching can be effected safely without entry of the regenerating liquid into the human body or without contact between the regenerating liquid and the body fluid.

The alternating and repeated use of the treating units A1 and A2 not only enables to drastically decrease the amount of the adsorbent to be used, but also helps to reduce the volume of the treating device and minimize the extracorporeal circulation volume of the blood.

Figure 3:
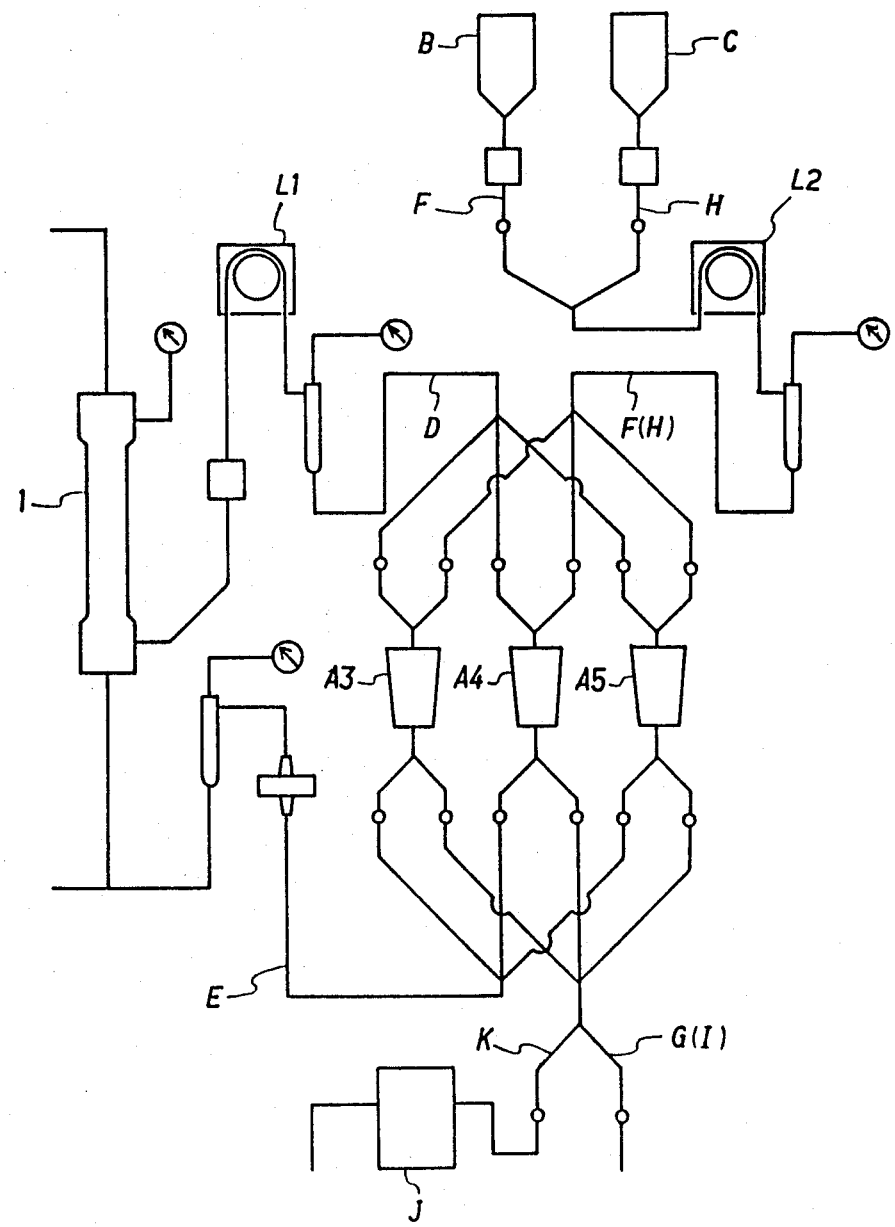

The above embodiment employs two treating units but it is, of course, possible to provide three or more treating units within the treating block. As for example, an embodiment comprising three treating units, namely first unit A3, second unit A4 and third unit A5, is shown in FIG. 3. In this embodiment, the treating units A3, A4 and A5 are used for the treatment in succession and repetition in the order of the first, second and third units, provided that the following steps (a) and (b) are added to the above-mentioned steps.

(a) When the amount of the body fluid treated by the first unit A3 has reached a predetermined level, the supply of the body fluid is switched to the second unit A4. The regeneration of the first unit A3 is performed simultaneously with the treatment of body fluid by the second unit A4.

(b) When the amount of the body fluid treated by the second unit A4 has reached a predetermined level, the supply of the body fluid is switched to the third unit A5. The regeneration of the second unit A4 is performed simultaneously with the treatment of the body fluid by the third unit A5.

The regeneration and washing of the first unit A3 are to be completed only by the time when the treatment of the body fluid by the third unit A5 is completed.

While the invention has been described with reference to preferred embodiments thereof, it is to be understood that the invention is not limited thereto but various changes and modifications may be made without departing from the scope of the invention. It is also possible to apply the invention to various other body fluids, of course.

The present invention offers the following advantages.

(1) Since the treating units can be reused, it is possible to make the volume of the treating unit smaller than that of a conventional treating unit so as to decrease the volume of the body fluid to be extracorporeally circulated. Therefore, with the body fluid treating apparatus according to the present invention, even underweight or hypotensive patients can be successfully treated.

(2) With the use of a smaller amount of adsorbent, a comparable or even a greater body fluid treating capacity can be realized in comparison with the prior art, thus contributing to a reduced cost of health care.

(3) When the regenerated treating unit is reused, line switching is made after confirming that the regenerating liquid has been thoroughly discharged and the salt concentration in the treating unit has returned to the physiological level. Therefore, there is no risk of entry of the regenerating liquid into the human body, nor does it happen that the body fluid contacts the regenerating liquid to raise the salt concentration of the body fluid. That is, a safe switching of circuit lines is assured.

(4) The present invention includes a highly reliable safety confirmation means when the line switching is automatically carried out in accordance with a computer program. When computer control is adopted, line switching is generally carried out automatically on the basis of the flow rate of body fluids or time data of passing body fluids. In that case, the safety can be further raised by confirming the validity or invalidity of any switching action again at a predetermined switching time.

Thus, the present invention provides a body fluid treating circuit method which reduces the burden on the patients and is safe to the patients.

What we claim is:

1. A method for treating a body fluid in an extracorporeal circuit consisting essentially of a body fluid collecting block, a body fluid treating block and a body fluid return block, said body fluid treating block including a plurality of treating units connected in parallel to each other and comprising at least one first-stage treating unit and at least one second-stage treating unit, which comprises:

(a) a first-stage treating step comprising feeding a body fluid to said first-stage treating unit, subjecting the body fluid to a predetermined treatment therein, and sending the treated body fluid to said body fluid return block;

(b) a feed line switching step which comprises switching the route of feed of the body fluid from said first-stage treating unit to said second-stage treating unit when the amount of the body fluid treated in said first-stage treating unit has reached a predetermined level;

(c) a body fluid sending step which comprises feeding a washing liquid to said first-stage treating unit to force out the body fluid present therein from said first-stage unit to said body fluid return block;

(d) a discharge line connecting step which comprises switching the line on the downstream side of said first-stage unit into communication with a discharge line when the first-stage treating unit has been purged of the body fluid by and filled with the washing liquid;

(e) a regenerating liquid feeding step which comprises feeding a predetermined amount of regenerating liquid to said first-stage treating unit filled with the washing liquid, and discharging the effluent from said first-stage treating unit outside the circuit;

(f) a regenerating liquid discharging step which comprises feeding the washing liquid to said first-stage treating unit to which the regenerating liquid has been fed in the step (e), thereby forcing out the regenerating liquid from said first-stage unit and discharging it outside the circuit;

(g) a washing step which comprises feeding a predetermined additional amount of the washing liquid to said first-stage unit after withdrawal of the regenerating liquid from said first-stage unit conducted in the step (f);

(h) a confirmation step which, after said washing step (g), comprises feeding the washing liquid further to said first-stage unit and guiding the effluent from said first-stage unit to a salt concentration measuring means for confirming if the salt concentration of said effluent is within a predetermined range;

(i) a washing liquid discharging step which comprises feeding a body fluid to the second-stage treating unit previously filled with the washing liquid, thereby forcing out the washing liquid from the second-stage treating unit and discharging it outside the circuit;

(j) a return line connecting step which comprises switching the line on the downstream side of said second-stage treating line into communication with a body fluid return line when the second-stage unit has been purged of the washing liquid and filled with the body fluid;

(k) a second-stage treating step which comprises feeding the body fluid further to said second-stage treating unit, subjecting it to the predetermined treatment therein, and sending the treated body fluid to the body fluid return block;

(l) a feed line re-switching step which comprises switching the route of feed of the body fluid to be treated from the second-stage treating unit to the first-stage treating unit when the amount of the body fluid treated in the second-stage unit has reached a predetermined level;

(m) a switching preparation step which comprises performing said washing liquid discharging step (i) with respect to the first-stage processing unit and, simultaneously, performing said body fluid discharging step (c) with respect to the second stage treating unit;

(n) a return line re-switching step which comprises switching the line on the downstream side of the first-stage treating unit from the discharge line to the body fluid return line while conducting said confirmation step (h) and, at the same time, switching the line on the downstream side of the second-stage treating unit into communication with the discharge line to interrupt said downstream side from the body fluid return line; and (o) a repeated first-stage treating step which comprises performing said first-stage treating step (a) again.

2. The method of claim 1, wherein said plurality of treating units are alternately and repeatedly used for the treatment.

3. The method of claim 1, wherein said body fluid treated in the treating units is a plasma fraction of blood separated by a plasma separator.

4. The method of claim 3, wherein after the completion of the treatment, the plasma fraction remaining in the treating block is guided to the plasma separator and caused to pass through the plasma separator in the direction reverse to the separation of plasma, thereby recovering blood corpuscles deposited onto the plasma separator.

* * * * *